Jan. 3 , 1956 E. PARISH Plant Pat. 1,442

STRAWBERRY PLANT

Filed April 20, 1954

Inventor

*Edith Parish*

By William E. Lucas

Attorney

United States Patent Office

Plant Pat. 1,442
Patented Jan. 3, 1956

1,442

STRAWBERRY PLANT

Edith Parish, Smelser Township, Grant County, Wis.

Application April 20, 1954, Serial No. 424,538

1 Claim. (Cl. 47—62)

My invention relates to a new and distinct variety of strawberry plant of the June bearing variety. The mother plant was discovered by me on my farm near Platteville, Wisconsin, growing between beds of Dunlap and Ambrosia strawberry plants, neither of which is patented. I am unable to assert whether the mother plant was a sport or mutation of either of said varieties or cross between the two.

The parent plant of my new variety had such unique and distinct characteristics that, on my said farm near Platteville, Wisconsin, I asexually reproduced it by transplanting rooted runners produced by it. For successive generations, at the same place, I continued the usual asexual reproduction by crown division and transplanting rooted runners until I had a bed of from 12,000 to 15,000 plants of the new variety.

Each successive plant has the same distinctive and unique characteristics exhibited by the mother ancestor.

The object of my asexual propagation was to develop a sufficient number of fruit-bearing plants so that I might judge of the quality of berry produced; determine the ability of the plant to withstand extremes of temperature (varying from 100° F. to minus 42° F.), periods of drought alternating with excessive moisture and humidity, and resistance to disease. The result of my discovery and asexual propagation has been the development of a distinctly new variety of strawberry plant embodying desirable characteristics not heretofore known.

In the accompanying drawings are illustrated three berries, a leaf, a leaflet, and the cross section of two additional berries; all of typical size and shape. In said drawings:

Figure 1 illustrates a typical leaf;

Figure 2 illustrates a typical terminal leaflet;

I refer now more specifically to the distinguishing characteristics of my new variety of June bearing strawberry plant and its fruit, which characteristics have been persistent through successive generations in over 10,000 plants, and which characteristics combine to distinguish my new variety from other known varieties.

Among the most unique characteristics are a large berry, rich in flavor and aroma, with non-fibrous flesh, without any noticeable core; sturdy, erect leaf and flower stems, the former bearing a plurality of leaflets which do not overlap; and indented akenes on the fruit. Important, too, from the standpoint of propagation and eventual fruit production are the numerous rooting runners produced, 14 or 15 being usual. Other distinguishing characteristics appear in the detailed summary hereafter given.

The berry is medium dark red, high in flavor and aroma, and sweeter than average. It ripens in my locality (approximately 42° 30′ north) from mid-June to early July, depending on the season; and the cropping season lasts from nineteen to twenty-one days. The ripening season is later than the Premier variety, and earlier than either Catskill or Robinson, neither of which is patented. Berries are large and borne prolifically. Terminal berries often weigh an ounce and a half; and berries weighing an ounce are common.

Below, I summarize a detailed description of this new variety of strawberry plant:

Size: Medium.

Roots: Long, vigorous.

Leaves: Medium green in color, with a glossy top surface slightly cupped.

Leaflets: Usually three, occasionally four, seldom five. The leaflets do not overlap. The terminal leaflet is large and broad. A typical terminal leaflet measures 3 inches in length and 1 5/16 inches in width.

Leaf stems: Stout and erect. From the crown to the tip of the terminal leaflet, is from 10 to 12 inches.

Runners: Hardy and freely produced, 14 or 15 from a single plant.

Foliage: Dense, even the ripened fruit is almost obstructed from view.

Flower stems: Thick, and invariably upright; and sufficiently stout to hold the ripened fruit from the ground; but few berries touch the ground.

*Flower characteristics*

Blossoms: Perfect.

Calyx: Medium in size.

Sepals: Tend to curve upward.

*The fruit*

Figure 3:
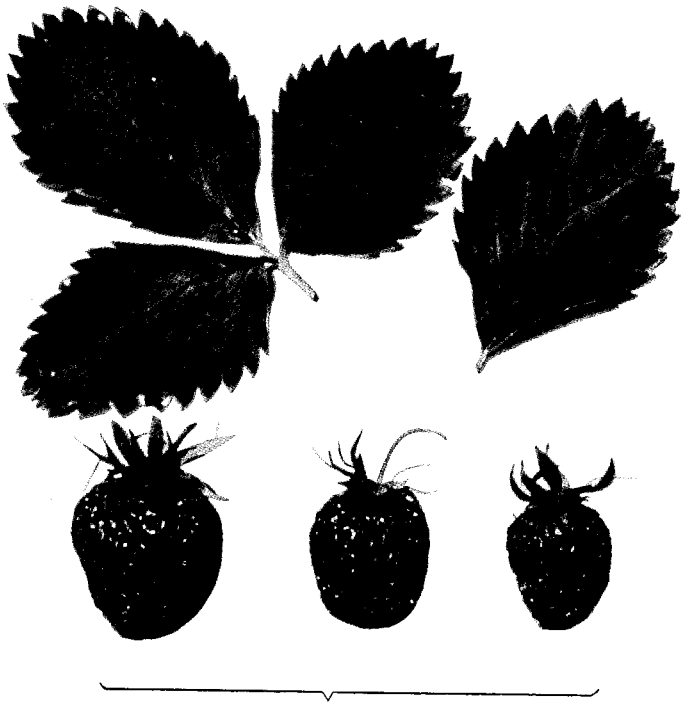
Figure 3 shows three typical berries.
Figure 4:
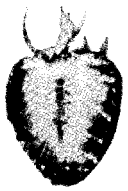
Figure 4 is a central vertical longitudinal section of a typical berry.
Figure 5:
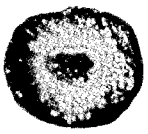
Figure 5 is a central horizontal section of a typical berry.

Size: Large. The left hand typical berry in Figure 3 measured 1¾ inches long and 1½ inches wide.

Shape: Wedge to frustro-conic.

Color: Outside color, medium dark red, even; when ripe the berry is red throughout, with a dark red center.

Flesh: Completely non-fibrous. Shades from medium dark red at the outside through lighter shades of red to a dark red center. There is no core and no hollow area or spot in the center.

Aspect: Glossy, waxy.

Seeds (akenes): Medium in number, yellow to red (depending on exposure), indented.

Flavor: Mild, sweeter than average, aromatic.

Uses: Home and local market. The berry cans, preserves, and freezes well; and as fresh fruit is an excellent keeper at room temperature.

My new variety of strawberry plant is distinguished from the variety known as "Catskill" by the presence of the following characteristics, none of which is found in Catskill: non-overlapping leaflets; no core, and no white or hollow center in the fruit; definitely indented seeds; early midseason bearing; prolific in production of runners; high in flavor and aroma. The leaves of my plant are less glossy and more rugose than those of the Catskill plant. The Catskill berry is irregular in shape. Those of my plant are wedge to frusto-conic in shape, but not irregular.

While the plant and the berry it produces may vary in some slight details, depending on weather and soil conditions, the characteristics herein given are typical.

What I claim is:

A new and distinct variety of strawberry plant substantially as herein shown and described, characterized by a large, coreless, non-fibrous berry, rich in flavor and aroma, and with indented seeds; by its sturdy, erect leaf and flower stems; and by its non-overlapping leaflets.

No references cited.